United States Patent [19]

Vogt

[11] 3,985,731

[45] Oct. 12, 1976

[54] 2H-2-BENZAZEPIN-1,3-DIONES

[75] Inventor: Berthold Richard Vogt, Yardley, Pa.

[73] Assignee: E. R. Squibb & Sons, Inc., Princeton, N.J.

[22] Filed: Mar. 28, 1975

[21] Appl. No.: 563,265

Related U.S. Application Data

[62] Division of Ser. No. 484,908, July 1, 1974, Pat. No. 3,887,544.

[52] U.S. Cl. .......................... 260/239.3 B; 424/244; 260/239.3 P
[51] Int. Cl.² ....................................... C07D 223/16
[58] Field of Search ............................. 260/239.3 B

[56] References Cited
UNITED STATES PATENTS

| | | |
|---|---|---|
| 3,225,031 | 12/1965 | Sherlock ........................ 260/239 BB |
| 3,242,164 | 3/1966 | Sherlock ........................ 260/239 BB |
| 3,409,607 | 11/1968 | Fujimura et al. .............. 260/239 BB |

OTHER PUBLICATIONS

Walker "J. Org. Chem." vol. 37, No. 24, (1972).

Walker et al. "J. Org. Chem." vol. 36, No. 3 (1971).

Primary Examiner—Henry R. Jiles
Assistant Examiner—Robert T. Bond
Attorney, Agent, or Firm—Lawrence S. Levinson; Merle J. Smith; Burton Rodney

[57] ABSTRACT

A compound of the formula

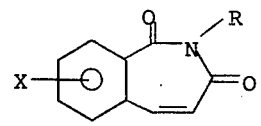

wherein X and R are as defined hereinafter, at least one of X and R being other than hydrogen, are provided and which are useful as central nervous system stimulants and for inducing increased motor activity as well as in vitro antimicrobial agents.

8 Claims, No Drawings

2H-2-BENZAZEPIN-1,3-DIONES

REFERENCE TO OTHER APPLICATIONS

This application is a division of application Ser. No. 484,908 filed July 1, 1974, now U.S. Pat. No. 3,887,544.

OBJECTS OF THE INVENTION

It is an object of the present invention to provide novel compounds which are sunscreen agents and CNS active agents. Another object is to provide a method for preparing these compounds. These and other objects of the present invention will be apparent from the following description.

SUMMARY OF THE INVENTION

Compounds of the formula

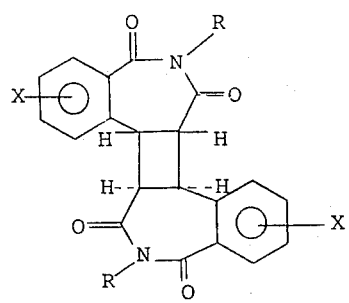

1

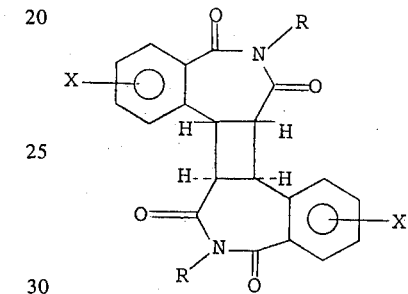

1

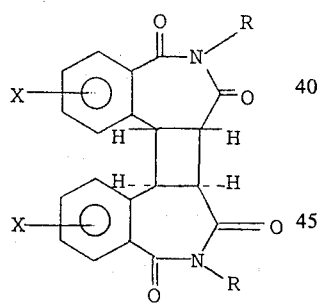

2 wherein X is an alkyl radical of from 1 to 4 carbon atoms, an alkoxy radical of from 1 to 4 carbon atoms, halogen (F, Cl, Br or I), preferably F and Cl, CF$_3$, or nitro, and wherein R is H, an alkyl radical of from 1 to 4 carbon atoms, an allyl radical or a dialkylaminoalkyl radical wherein the alkyl radical is from 1 to 3 carbon atoms and wherein each alkyl group of the dialkylamino radical has from 1 to 3 carbon atoms, are CNS active agents.

DETAILED DESCRIPTION

The compounds of the present invention may be prepared by treating with ultraviolet radiation (of from about 200 to about 380 m$\mu$ in wavelength) a compound of the formula

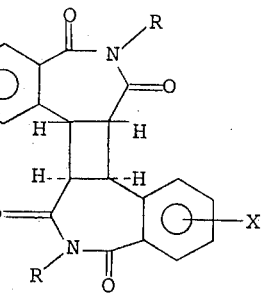

3 wherein X is H, alkyl of from 1 to 4 carbon atoms, alkoxy, halogen, CF$_3$, or NO$_2$, and wherein R is H, alkyl of from 1 to 4 carbon atoms, allyl or dialkylaminoalkyl wherein each alkyl group may have from 1 to 3 carbon atoms. The reaction is carried out in an essentially inert hydrocarbon solvent, e.g., benzene, hexane or cyclohexane. The irradiation can result in a mixture of isomers of the formulas

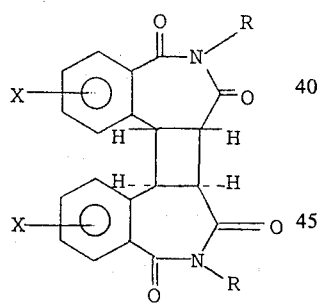

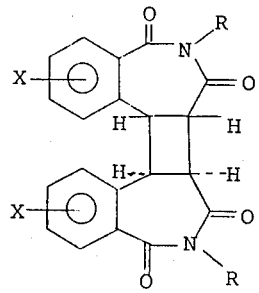

2

Generally, the "head-to-tail" isomer 1 predominates over the "head-to-head" isomer 2. A compound of formula 1 wherein R is other than hydrogen may also be prepared by reacting a compound of formula 1 wherein R is hydrogen with an appropriate base, such as thallous ethoxide, NaH or K-t-butoxide and reacting the resultant salt with the appropriate alkylating agent, such as

R-Z      4 wherein R is as defined above, excepting hydrogen, and Z is a suitable leaving group such as chlorine, bromine, iodine, alkyl sulfonate or aryl sulfonate. This reaction may be carried out in an optional, essentially non-reactive organic solvent such as hexamethylphosphorus triamide, dimethylformamide, dimethyl sulfoxide, 1,2-dimethoxyethane, benzene, toluene or xylene. A compound of formula 3 wherein R is other than hydrogen is obtained by treating a compound of the formula

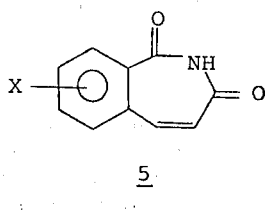

5 with an appropriate base, such as thallous ethoxide, NaH or K-t-butoxide and reacting the resultant salt with the appropriate alkylating agent, such as

R-Z        4 wherein R is as defined above, excepting hydrogen, and Z is a suitable leaving group such as chlorine, bromine, iodine, alkyl sulfonate or aryl sulfonate. This reaction may be carried out in an optional, essentialy non-reactive organic solvent such as hexamethylphosphorus triamide, dimethylformamide, dimethyl sulfoxide, 1,2-dimethoxyethane, benzene, toluene or xylene. A compound of formula 5 is prepared by treating compounds of formula

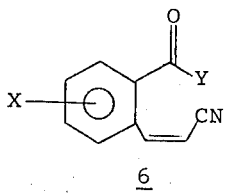

6 wherein, Y is chlorine or bromine, with an appropriate acid catalyst, such as hydrogen chloride, in an inert aprotic organic solvent, such as 1,2-dimethoxyethane, followed by hydrolysis gives the compound of formula 5.

A compound of formula 5 is also produced by reacting compounds of formula 7

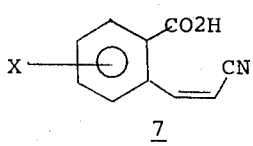

7 with an appropriate acid, such as polyphosphoric acid, at from 20° to 200° C.

A compound of formula 6 is prepared by reacting a compound of formula

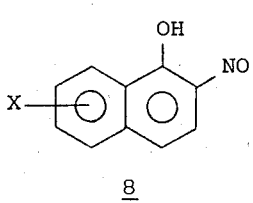

8 with an appropriate phosphorus halide, such as phosphorus pentachloride, in an inert organic solvent such as hexane or cyclohexane at from about 20° to about 150° C.

A compound of formula 7 is prepared by hydrolyzing a compound of formula 6 in the optional presence of an apotic water miscible solvent, e.g., THF or 1,2-dimethoxyethane at a temperature of from about 0° to about 100° C.

A compound of formula 8 is prepared by methods well known to those versed in the art. Such methods include brominating an appropriate α-tetralone of formula

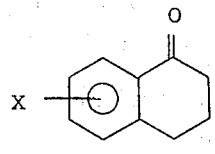

9 with bromine in carbon disulfide and subsequently reacting the resultant 2-bromo-α-tetralone of formula

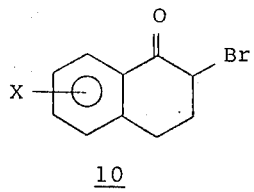

10 with anhydrous lithium chloride in dry dimethylformamide at reflux temperatures [cf. J. Amer. Chem. Soc., 572ff (1938) and J. Org. Chem., 24 992ff (1959)].

All reactions are carried out at room temperature, unless otherwise indicated.

The apparatus employed in irradiation reactions consists of a quartz well (Hanovia No. 19434) with a Pyrex filter immersed in a Pyrex reaction vessel having a capacity of 400 ml. The light source is a 450 watt (Hanovia No. 679A-36) mercury arc lamp. The apparatus is maintained at a temperature of from about 10° to about 50° with water cooling. The reaction is carried out under an inert atmosphere, such as argon or nitrogen.

The final compounds of the present invention possess the property of absorbing ultraviolet light and so are useful as sun screen agents. For this use they may be incorporated into various materials such as plastics and textiles, in known manner, to prevent or retard degradation due to ultraviolet light. The final compounds of the present invention of formula 1 wherein R is other than H are CNS depressants and have utility as muscle relaxants and analgesics. For this purpose they may be employed in mammalian species, e.g., rats and mice in a dosage level of from about 25 to about 200 mg/kg per day in one dose or in up to 4 divided doses. Final products of the present invention of formula 2 wherein R is other than H are CNS stimulants and have utility as anorectics, and antinarcoleptic. For this purpose they may be employed in mammalian species, e.g., rats and mice in a dosage level of from about 25 to about 200 mg/kg per day in one dose or in up to 4 divided doses. Final products of the present invention wherein R is hydrogen are intermediates for those final products wherein R is alkyl of from 1 to 4 carbons.

Some of the monomeric intermediates for the final products of the present invention are biologically active in themselves. Thus, the novel compounds of the following formula wherein R is other than H

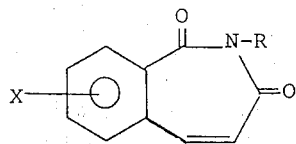

are CNS stimulants and induce increased motor activity, and are also in vitro antimicrobial agents. In addition the compounds of the foregoing formula wherein R is alkyl are inhibitors of 3',5'-cyclic adenosine phosphodiesterase. These compounds are also CNS stimulants and exhibit increased motor activity and are also in vitro antifungal at a concentration of from about 6 to about 31 mcg/ml. Compounds of the foregoing formula wherein R is dialkylaminoalkyl are in vitro antifungal agents at a concentration of from about 50 to about 100 mcg/ml and in vivo anthemlmintic agents at a concentration of about 0.2%. The novel compounds of the foregoing formula wherein R is H and containing a chloro substituent in the 7 or 8 position are muscle relaxants and anxiolytic agents. Compounds wherein X is chloro in the 7-position are muscle relaxants at a dosage level of from about 12 to about 100 mg/kg while compounds wherein X is chloro in the 8-position are muscle relaxants at a dosage level of from about 25 to about 200 mg/kg. The compound of the foregoing formula wherein R is H and X is also H are CNS stimulants and exhibit increased motor activity at a concentration of from about 12 to about 100 mg/kg. This compound also exhibits in vitro antibacterial and antifungal activity at a concentration of from about 25 to about 75 mcg/ml.

The compounds of the present invention in the described dosages may be administered orally; however, other routes such asintraperitoneally, subcutaneously, intramuscularly or intravenously may be employed.

The active compounds of the present invention are orally administered, for example, with a inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a distintegrating agent such as corn starch, potato starch, alginic acid and the like; a lubricant such as magnesium stearate, and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples illustrate the present invention without, however, limiting the same thereto. All temperatures are expressed in degrees Centigrade.

EXAMPLE 1

7a,7b:14a:14b-trans-7a,7b,14a,14b-Tetrahydrocyclobuta[1,2-d:3,4-d']bis[2]benzazepine-5,7-12,14(6H,13H)-tetrone A. 2-(Chloroformyl)-cis-cinnamonitrile (I)

To a rapidly stirring suspension of phosphorus pentachloride (197.5 g) in dry hexane (3.5 liters) is added 167.0 g (0.964 mole) of 2-nitroso-1-naphthol. The mixture is stirred at room temperature for 1 hour after which it is refluxed for 1 hour, cooled slightly and decanted while hot. The residue is boiled with hexane (3.0 liters) for another hour after which the solution is decanted and combined with the first hexane extract. It is evaporated down to dryness. Yield: 200.0 g (crude). This residue is extracted with hexane (2.0 liters), the hexane decanted, cooled, and the resultant crystals are filtered off. The filtrate is used to reestract additional compound from the above residue (the reextraction being repeated four times) with cooling and filtering of the crystals obtained each time. Yield: 79.0 g (42.5%), mp=72°–74°.

B. 3-Hydroxy-1H-2-benzazepin-1-one 59.0 g (0.308 mole) of (I) is taken up in dry dioxane (800 ml) and purged with HCl gas at 70° for 5 hours. Solvent is removed, the residue is azeotropically distilled three times with benzene and the residue taken up in dimethoxyethane (200 ml) and water (22 ml). After standing overnight at room temperature, the reaction mixture is evaporated to dryness, taken up in ethyl acetate (1.5 liters) and washed twice with saturated $NaHCO_3$ solution (630 ml portions). The $NaHCO_3$ phase is back-washed with ethyl acetate (1.0 liter), the organic extracts are combined and washed 3 times with 500 ml portions of water. The organic layer is evaporated. The solid obtained is taken up in acetone (1.0 liter), charcoaled and evaporated. The product is recrystallized from benzene (500 ml) and petroleum ether (650 ml). Yield: 20.7 g, percent yield: 36.9%, single spot, Rf 0.30 (alumina, $CHCl_3$:EtOAc-6:4). mp=129°–131° (crude); mp on recrystallization: 135°–136°.

C. 7a,7b:14a:14b-trans-7a,7b,14a, 14b-Tetrahydrocyclobuta[1,2-d:3,4-d']bis[2]benzazepine-5,7-12,14(6H,13H)-tetrone 1.58 g of 3-hydroxy-1H-2-benzazepin-1-one in 250 ml of spectral grade benzene is purged with nitrogen and then irradiated in the previously described irradiation apparatus for 3 hours. The product is filtered off and extracted in a Soxhlet extractor with 400 ml of acetone. The acetone extract is filtered and evaporated to give 1.02 g (70%) of the title compound.

Recrystallization from acetone gives 0.75 g of pure product. mp (dependent on rate of heating); shrinks at ca, 250°, darkens at ca, 315°, decomposes at 336°–345°.

EXAMPLE 2

7a,7b:14a,14b-trans-7aa,7b,14a,14b-tetrahydro-6,13-dimethylcyclobuta[1,2-d:3,4-d']bis[2]benzazepine-5,7,12,14(6H,13H)-tetrone

A. 2-Methyl-2H-2-benzazepin-1,3-dione 3.0 g (0.0173 mole) of 3-hydroxy-1H-2-benzazepin-1-one is stirred with 1.25 equivalents of thallous ethoxide (5.4 g) in dry tetrahydrofuran (75 ml) for 30 minutes. The precipitate is filtered, washed with ether and dried in vacuo. Yield: 6.42 g (I).

The thallium salt (I) is then suspended in methyl iodide (60 ml) and refluxed under argon for 5 hours. The methyl iodide is blown off in the hood and the resulting solid stirred for a few minutes in benzene (100 ml). The yellow precipitate is filtered off, washed with another 100 ml of benzene and the combined filtrates passed through a Florisil column (1 inch × 5 inches). The column is washed with 500 ml benzene and the eluate evaporated to dryness. Yield: 2.76 g, 85.20%; mp 67°–68°. The product is recrystallized from a minimum amount of ethanol and water. Yield: 2.6 g, mp 67°–68°.

B. 7a,7b:14a,14b-trans-7a,14a,14b-tetrahydro-6,13-dimethylcyclobuta[1,2-d:3,4-d']bis[2]-benzazepine-5,7,12,14(6H,13H)-tetrone 2.63 g of the product from part A in ca 750 ml of spectral grade benzene is purged with nitrogen for 10 minutes and irradiated as described in example 1 part C for 6 hours. After concentrating to ca 50 ml, the suspension is treated with 55 ml hexane, in a dropwise fashion. The precipitate is filtered off, dried and chromatographed on 36 g of Woelm silica gel (18 × 292 mm column) starting with 1000 ml of methylene chloride, followed by 200 ml of methylene chloride-chloroform (1:1) and then 200 ml of chloroform. These fractions are collected and discarded, and the next 600 ml of chloroform are evaporated to give 2.06 g (80%) of the title compound. Recrystallization (at −20° C) from ca 1.2 liters of boiling absolute ethanol gives 0.45 g of pure product, mp 273°–274°.

EXAMPLE 3

7a,7b:14b,14c-trans-7a,7b,14b,14c-Tetrahydro-6,9-dimethylcyclobuta[1,2-d:4,3-d']bis[2]benzazepine-5,7,8,10(6H,9H)-tetrone

The filtration remaining after recrystallization from ethanol of the final product of example 2 is concentrated to about 800 ml, cooled at −20° and filtered; the filtrate is concentrated to about 500 ml, cooled at −20° and filtered. This filtrate is concentrated to about 75 ml, cooled at −20° and the title compound filtered off and dried, mp 222°–224°, wt 0.33 g.

EXAMPLE 4

7a,7b:14a,14b-3,10-dichloro-trans-7a,7b,14a,14b-Tetrahydrocyclobuta[1,2-d:3,4-d']bis[2]benzazepine-5,7,12,14(6H,13H)-tetrone

A. β-(p-Chlorobenzoyl)-propionic Acid (I)

To a solution of 280 g (2.8 moles) of sucinnic acid in chlorobenzene (1.0 liter, 4 equivalents) in a 5-liter 3-neck flask, is added 900 g (6.7 moles) of anhydrous aluminum chloride over a period of 20 minutes with stirring. The reaction mixture is then heated at 100° for 3 hours. The resulting solution is cooled in an ice bath and treated cautiously with water (1.2 liters), followed by concentrated hydrochloric acid (500 ml). The reaction mixture is steam distilled to remove the excess chlorobenzene and the hot residual acid is transferred to two 2-liter beakers. Upon cooling in an ice bath, the product solidifies. The solid is stirred with dilute hydrochloric acid (1.0 liter, 1:3 v/v) and the precipitate is filtered off and washed with 1.0 liter of cold water.

The crude acid is then dissolved in aqueous sodium carbonate (420 g in 2.5 liter of water), boiled cautiously for 15 minutes, filtered while hot and the hot filtrate treated with activated carbon for 30 minutes. The carbon is filtered, washed with 2.0 liters of hot water and the filtrates are combined and acidified with concentrated hydrochloric acid (250 ml) to pH 2. The acidified solution is cooled in an ice bath and the white precipitate is filtered and washed with 2.0 liters of cold water. The product is air dried. Yield: 384.7 g (64.61%), mp 129°–132°.

B. α-(p-Chlorophenyl)-butyric acid (II)

A 5-liter, 3-neck flask is charged with 400 g (1.9 moles) of (I), 350 g potassium hydroxide, 2.47 liters of ethylene glycol and 155 g of 95% hydrazine diluted to 250 ml with water. The mixture is refluxed for 1.5 hours, after which the water is drained from the condenser and the internal temperature of the reaction mixture is allowed to rise to 190°. Refluxing is then continued for another 4 hours. The cooled solution is diluted with 2.5 liters of water and poured slowly into 2.0 liters of 6N hydrochloric acid. The precipitate is filtered and air-dried. Yield: 332.5 g, 88.1%, mp 54°–57°.

The crude product is recrystallized from hexane (3.0 liters). Yield: 273.5 g, mp 35°–37°; light cream solid.

C. 7-Chloro-1-tetralone (III)

101 g (0.51 mole) of (II) is added to 1.25 kg polyphosphoric acid and the mixture is heated to 70° with stirring. The temperature rises spontaneously so heating is reduced, maintaining an internal temperature between 90°–100° for a total reaction time of one hour. The rust-colored solution is poured into 1.2 liters of ice water, stirred for 30 minutes and the crude product is filtered. The light yellow product is then taken up in ether (2.0 liters) and washed successively with water (1.0 liter), 5% sodium hydroxide (1.0 liter), water (1.0 liter), 5% acetic acid (500 ml), 5% sodium bicarbonate (500 ml) and water (1.0 liter). The organic phase is dried over anhydrous sodium sulfate, filtered and evaporated. Yield: 82.0 g (89.3%), mp 92°–93°. The product is dried overnight in vacuo at room temperature.

D. 2-Bromo-7-chloro-1-tetralone (IV)

To a solution of 7-chloro-1-tetralone, 204.3 g, (1.1 moles), in carbon disulfide (1.08 liters) there is dropwise, with stirring, 176 g (1.1 moles) of bromine in 540 ml carbon disulfide at 0°–5° C. After stirring for an additional 30 minutes, the solvent is removed, giving a dark brown syrup, weighing 315 g. The crude product is used as is in the following step.

E. 7-Chloro-1-naphthol (V)

A solution of lithium chloride, 146.3 g (3.45 moles) in dry dimethylformamide (3.4 liter) is prepared with slight heating to promote solution. To this is then added (IV) in 1.13 liters of dry dimethylformamide and the reaction mixture is refluxed for 27 hours under an atmosphere of argon. The reaction mixture is cooled and diluted with 3.38 liters of water, and extracted with ether (7.0 liters). The aqueous phase is diluted with an equal volume of water and extracted with an additional 2.5 liters of ether. The organic extracts are combined and washed four times with 6.0 liter portions of water. The organic phase is dried over anhydrous magnesium sulfate, filtered and evaporated. Yield: 207.14 g, mp 117°–119°.

F. 7-Chloro-2-nitroso-1-naphthol (VI)

To a solution of sodium hydroxide, 22.4 g in 1.0 liter of water, is added 100 g (0.56 mole) of the chloronaphthol (V). The mixture is stirred with slight heating until solution is complete. The solution is then cooled to −5° to 0° and treated with sodium nitrite, 40.0 g, (0.6 mole) followed by the addition of concentrated sulfuric acid (176 ml) over a 90-minute period. Ice-water (600 ml) is added periodically to prevent clumping of the solid which forms. When addition of the acid is complete, the reaction mixture is stirred for another hour at −5° to 0°. The product is filtered, washed with 4.0 liters of cold water, air-dried overnight and then dried in vacuum oven at 60° for 2.5 days. Yield: 108.6 g (93.4%) light yellow-green solid.

G. 4-Chloro-2-(chloroformyl)-cis-cinnamonitrile (VII)

To a rapidly stirring suspension of phosphorus pentachloride (150.0 g) in dry hexane (2.6 liters) is added 156.4 g (0.72 mole) of 7-chloro-2-nitroso-1-naphthol (VI). The mixture is stirred at room temperature for 1 hour after which it is refluxed for 2 hours. The hexane solution is decanted while hot, 2.0 liters of dry hexane are added to the residue in the flask, and refluxed for another hour. The hexane solution is decanted, combined with the first hexane extract and evaporated to dryness. Yield: 100 g, semi-solid dark brown residue. The crude product is extracted with 2.0 liters of hot dry hexane. The hot supernatant solution is decanted from the tarry residue at the bottom of the flask, concentrated to a volume of 700 ml and cooled in an ice bath. Repeated extractions of the original residue and tarry material are done with a total of 3.0 liters of hexane. All of the extracts are concentrated, cooled in an ice bath, and the product filtered off and dried. Total yield: 51.1 g (31.4%), mp 71°–74°.

H. 8-Chloro-2H-2-benzazepine-1,3(2H)-dione (VIII)

A solution of 25.0 g (0.11 mole) of (VII) in dry dioxane (275 l ml) is purged with hydrogen chloride gas for 5 hours at 70° with the exclusion of moisture. The reaction mixture is cooled and evaporated. The residue is distilled azeotropically three times with benzene, taken up in a solution of 380 ml dimethoxyethane and 30 ml water and stirred overnight.

The suspension is evaporated and the residue taken up in ethyl acetate (2.5 liters). The organic phase is washed twice with 500 ml portions of 5% sodium bicarbonate. At this point, solid material, which is not soluble in either phase is filtered off.

The organic layer is washed twice with 500 ml portions of water, and both the bicarbonate and aqueous extracts are backwashed with ethyl acetate (500 ml). The organic extracts are combined, dried over anhydrous sodium sulfate, filtered and evaporated. The residue is stirred with a small amount of methanol containing 5% sodium bicarbonate. The suspension is filtered and the filter cake washed with water and dried to yield 6.0 g of partially purified product. 4.0 g of the partially purified product is dissolved in tetrahydrofuran (120 ml) with heating, treated with activated carbon and the suspension filtered. The light yellow filtrate is concentraated to 40 ml and cooled to yield 2.43 g (68.3%), of title compound, mp 235.0° to 236.5°.

I. 7a,7b:14a,14b-3,10-dichloro-trans-7a,7b,14a,14b-Tetrahydrocyclobuta[1,2-d:3,4-d']bis[2]benzazepine-5,7,12,14(6H,13H)-tetrone The product (VIII) from part H is treated as described in part C of example 1 to yield the title compound.

EXAMPLE 5

7a,7b:14a,14b-6,13-[3-(Dimethylamino)propyl]-trans-7a,7b,14a,14b-tetrahydro-cyclobuta[1,2-d:3,4-d']-bis[2]-benzazapine-5,7,12,14(6H,13H)-tetrone A. 2-[3-(Dimethylamino)propyl]-2H-2-benzazepine-1,3-dione, fumarate salt 3.0 g (0.0173 mole) of 3-hydroxy-1H-2-benzazepin-1-one is dissolved in dry tetrahydrofuran (58 ml) and treated with 5.38 g (.0216 mole) of thallous ethoxide. The resulting suspension is stirred for 15 minutes, filtered and the precipitate washed with ether. The thallium salt obtained is dried under vacuum for 30 minutes. Yield: 6.35 g, mp 197°–203° (I).

Meanwhile, 3-(dimethylamino)propyl chloride hydrochloride (3.56 g, 0.0225 mole) is suspended in 112 ml toluene and shaken with a solution of 5.9 g KOH in 5.9 ml water. The organic phase is separated, dried over 4A molecular sieves for 30 minutes and then added, dropwise over a 30 minute period, to a suspension of the thallium salt (I) in toluene (150 ml) at reflux. The reaction is refluxed for 3 hours under argon after which time another 3.56 g of the 3-(dimethylamino)propyl chloride alkylating agent is added. Refluxing is continued for an additional 3 hours, the reaction mixture is cooled and filtered through celite. The celite is washed with 100 ml toluene, the washings and filtrate combined and the solution passed through a Florisil column (1-¼inches × 4 inches). The column is washed with benzene (600 ml) and the light yellow eluant evaporated to dryness. The residual product is taken up in 60 ml acetone and mixed with a solution of 1.51 g (0.0127 mole) of fumaric acid in 120 ml acetone. The clear solution is evaporated to dryness. The resultant crude product is recrystallized first from a minimal amount of acetone and then from hot absolute ethanol (25 ml) to give the pure product. Yield 2.37 g, mp 116°–117°. Second crop: 1.71 g.

B. 7a,7b:14a,14b-trans-7a,7b,14a,14b-Tetrahydro-6,13-[3-(dimethylamino)propyl]-cyclobuta[1,2-d:3,4-d']bis[2]benzazepine-5,7,12,14(6H,13H)-tetrone The product from part A above is treated as described in part C of example 1 to yield the title compound.

EXAMPLE 6

7a,7b:14a,14b-2,9-Dichloro-trans-7a,7b,14a,14b-tetrahydro-cyclobuta[1,2-d:3,4-d']bis[2]benzazepine-5,7,12,14(6H,13H)-tetrone A. 6-Chloro-2-nitroso-1-naphthol (I)

A solution of 70.0 g (0.39 mole) of 6-chloro-1-naphthol in aqueous sodium hydroxide, 15.6 g (0.39 mole) of sodium hydroxide in 1.35 liters of water is prepared by warming the mixture on a steam bath. The resulting solution is cooled to −5° to 0° and 28.0 g (0.40 mole) of sodium nitrite are added followed by the addition of 216.6 ml of 11.3 N sulfuric acid (sp. gr. 1.32) over a 90-minute period. Ice-water, 1.0 liters, is added from time to time to prevent aggregation of the precipitate that forms. The mixture is stirred an additional hour after addition is completed, the precipitate filtered off and washed with 1.5 liter of ice-water.

The product is dried overnight in vacuo after which it is dried for an additional hour over phosphorus pentoxide. Yield: 78.03 g (96%), mp 198° dec.

B. 5-Chloro-2-(chloroformyl)-cis-cinnamonitrile (II)

To a rapidly stirring suspension of phosphorus pentachloride, 68.0 g, 0.326 mole in dry hexane (1.6 liters) is added 78.03 g (0.322 mole) of 6-chloro-2-nitroso-1-naphthol (I). The mixture is stirred at room temperature for 3 hours, the refluxed for 2 hours. The warm solution is then decanted and the residue in the reaction vessel refluxed for another hour with 1.0 liter of dry hexane. The hexane extracts are combined and evaporated to dryness. Yield: 75.0 g semi-solid brown residue. This crude product is recrystallized by taking it up in 2.0 liters of hot hexane, evaporating the solution down to a minimum volume (ca 300 ml) and cooling in an ice-water bath. Yield 31.0 g (42.59%).

C. 7-Chloro-3-hydroxy-1H-2-benzazepin-1-one (III)

A solution of 15.0 g (0.066 mole) of the cinnamonitrile (II) in dry dioxane (165 ml) is purged with hydrogen chloride gas for 5 hours at 70°C, with the exclusion of moisture, after which it is cooled and evaporated to dryness. The residue is distilled azeotropically three times with benzene, taken up in dimethoxyethylene (175 ml) and water (60 ml) and kept at room temperarture for 2 days. The mixture is evaporated to dryness, the residue is taken up in ethyl acetate (2.5 liters) and the solution is extracted with two 300 ml portions of 5% sodium bicarbonate solution.

The crude product, which is insoluble in both phases, is filtered off. Yield: 5.71 mp 260°–262°.

4.0 g of this material is taken up in hot tetrahydrofuran (200 ml), treated with activated carbon and filtered. The product precipitates in the filtrate and, after cooling in an ice-bath, is filtered off. Yield: 2.2 g, mp 263°–264°. The filtrate is concentrated down to 70 ml and gives a second crop of 864.3 mg., mp 263°–264°. (III).

D. 7a,7b:14a,14b-2,9-Dichloro-trans-7a,7b,14a,14b-tetrahydrocyclobuta[1,2-d']bis[2]benzazepine-5,7,12,14(6H,13H)-tetrone The product III from part C above is treated according to the procedure of part C of example 1 to yield the title compound.

EXAMPLES 7–23

Following the procedure of parts F, G, H and I of example 4, but substituting for 7-chloro-1-naphthol in part F, the compound listed in column I, there is obtained the correspondingly substituted compound of formula I, wherein the substituents occupy the positions given in column II, for the major isomer, and the positions given in column III, for the minor isomer (isolated as described in example 3).

|  | Column I | Column II | Column III |
| --- | --- | --- | --- |
| 7. | 8-chloro-1-naphthol | 4,11-dichloro | 4,11-dichloro |
| 8. | 5-chloro-1-naphthol | 1,8-dichloro | 1,14-dichloro |
| 9. | 7-fluoro-1-naphthol | 3,10-difluoro | 3,12-difluoro |
| 10. | 8-nitro-1-naphthol | 4,11-dinitro | 4,11-dinitro |
| 11. | 7-nitro-1-naphthol | 3,10-dinitro | 3,12-dinitro |
| 12. | 6-nitro-1-naphthol | 2,9-dinitro | 2,13-dinitro |
| 13. | 5-nitro-1-naphthol | 1,8-dinitro | 1,14-dinitro |
| 14. | 5-methyl-1-naphthol | 1,8-dimethyl | 1,14-dimethyl |
| 15. | 6-methyl-1-naphthol | 2,9-dimethyl | 2,13-dimethyl |
| 16. | 7-methyl-1-naphthol | 3,10-dimethyl | 3,12-dimethyl |
| 17. | 6-n-propyl-1-naphthol | 2,9-di-n-propyl | 2,13-di-n-propyl |
| 18. | 6-methoxy-1-naphthol | 2,9-dimethoxy | 2,13-dimethoxy |
| 19. | 7-methoxy-1-naphthol | 3,10-dimethoxy | 3,12-dimethoxy |
| 20. | 8-methoxy-1-naphthol | 4,11-dimethoxy | 4,11-dimethoxy |
| 21. | 6-n-butoxy-1-naphthol | 2,9-di-n-butoxy | 2,13-di-n-butoxy |
| 22. | 6-(trifluoromethyl)-1-naphthol | 2,9-bis(trifluoromethyl) | 2,3-bis(trifluoromethyl) |
| 23. | 7-(trifluoromethyl)-1-naphthol | 3,10-bis(trifluoromethyl) | 3,12-bis(trifluoromethyl) |

EXAMPLE 24

7a,7b:14a:14b-2,9-difluoro-trans-7a,7b,14a,14b-tetrahydrocyclobuta-[1,2-d:3,4-d']bis[2]benzazepine-5,7,12,14(6H,13H)-tetrone The title compound is obtained following the procedure of example 4, parts D, E, F, G, H and I, but substituting 6-fluoro-1-tetralone for 7-chloro-1-tetralone in part D.

EXAMPLE 25

7a,7b:14a,14b-trans-7a,7b,14a,14b-tetrahydro-6,13-dimethylcyclobuta[1,2-d:3,4-d']bis[2]benzazepine-5,7,12,14(6H,13H)-tetrone A stirred solution of 3.46 g (0.01 mole) of 7a,7b-14a,14b-trans-7a,7b,14a,14b-tetrahydrocyclobuta[1,2-d:3,4-d'[-bis[2]benzazepine-5,7,12,14(6H,13H)-tetraone in 140 ml of dimethylformamide is treated with 2.49 g (0.01 mole) of thallous ethoxide. After 1 hour, 300 ml of ether is added, the precipitated thallium salt (I) is filtered off and dried in vacuo for 2 hours.

The thallium salt (I) is then suspended in methyl iodide (60 ml), stirred at room temperature for 2 hours and then refluxed for 3 hours, all under argon. The reaction mixture is cooled, the methyliodide is blown off in the hood and the resulting solid stirred for 1 hour in methylene chloride. The precipitate is filtered off, washed with methylene chloride and the combined filtrates passed through a florisil column (1 inch × 5 inches). The column is washed with 500 ml chloroform and the eluate evaporated to dryness. The product is recrystallized from a minimum amount of absolute ethanol.

EXAMPLE 26

7a,7b:14a,14b-trans-7a,7b-tetrahydro-6,13-dimethylcyclobuta[1,2-d:3,4-d']bis[2]benzazepine-5,7,12,14(6H,13H)-tetrone 3.46 g (0.01 ml) of 7a,7b,14a,14b-trans-7a,7b,-14a,14b-tetrahydrocyclobuta[1,2-d:3,4-d']bis[2]benzazepine-5,7,12,14(6<u>H</u>,13<u>H</u>)-tetraone, 14 g of methyl iodide, 9 g of anhydrous calcium oxide and 1 g of Drierite in 50 ml of dry dimethyl sulfoxide are stirred for 8 hours. The precipitate was filtered off, the filtrate evaporated and the residue partitioned between methylene chloride and water. The organic phase is treated as described in Example 25 to give the product.

EXAMPLE 27

7a,7b:14a,14b-trans-7a,7b,14a,14b-tetrahydro-6,13-diallylcyclobuta[1,2-d:3,4-d']bis[2]benzazepine-5,7,12,14(6H,13H)-tetrone A. 2-Allyl-2<u>H</u>-benzazepin-1,3-dione 3.0 g (0.0173 mole) of 3-hydroxy-1<u>H</u>-2-benzazepin-1-one is stirred with 1.25 equivalents of thallous ethoxide (5.4 g) in dry tetrahydrofuran (75 ml) for 30 minutes. The precipitate is filtered, washed with ether and dried in vacuo. Yield: 6.42 g (I).

The thallium salt (I) is then suspended in allyl iodide (60 ml) and refluxed under argon for 5 hours. The allyl iodide is evaporated in the hood and the resulting solid stirred for a few minutes in benzene (100 ml). The yellow precipitate is filtered off, washed with another 100 ml of benzene and the combined filtrates passed through a Florisil column (1 inch × 5 inches). The column is washed with 500 ml benzene and the eluate evaporated to dryness. The residual product is recrystallized from a minimum amount of ethanol and water.

B. 7a,7b:14a,14b-trans-7a,7b,14a,14b-tetrahydro-6,13-diallylcyclobuta[1,2-d:3,4-d']bis[2]-benzazepine-5,7,12,14(6H,13H)-tetrone 2.63 g of the product from part A in ca 750 ml of spectral grade benzene is purged with nitrogen for 10 minutes and irradiated as described in example 1 part C for 6 hours. After concentrating to ca 50 ml, the suspension is treated with 55 ml hexane, in a dropwise fashion. The precipitate is filtered off, dried and chromatographed on 36 g of Woelm silica gel (18 × 292 mm column) starting with 1000 ml of methylene chloride followed by 200 ml of methylene chloride-chloroform (1:1) and then 800 ml of chloroform. These fractions are collected and evaporated to give the title compound. Recrystallization (at −20° C) from ca 1.2 liters of boiling absolute ethanol gives the title compound.

What is claimed is:

1. A compound of the formula

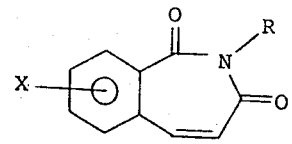

wherein X is hydrogen, alkyl of from 1 to 4 carbons, alkoxy of from 1 to 4 carbons, halogen, $CF_3$ or $NO_2$, and R is alkyl of from 1 to 4 carbons, allyl, dialkylaminoalkyl wherein each alkyl group may have from 1 to 3 carbon atoms or hydrogen, provided that when R is hydrogen X is other than hydrogen, and pharmaceutically acceptable acid addition salts thereof when R is dialkylamino alkyl as previously defined.

2. The compound as defined in claim 1 wherein R is alkyl.

3. The compound as defined in claim 1 wherein X is hydrogen and R is methyl.

4. The compound as defined in claim 1 wherein R is dialkylamino.

5. The compound as defined in claim 1 wherein R is $(CH_2)_3N(CH_3)_2$ and X is hydrogen.

6. The compound as defined in claim 1 wherein R is hydrogen and X is halogen.

7. The compound as defined in claim 6 wherein X is 8-Cl.

8. The compound as defined in claim 6 wherein X is 7-Cl.

* * * * *

UNITED STATES PATENT AND TRADEMARK OFFICE
CERTIFICATE OF CORRECTION

PATENT NO. : 3,985,731
DATED : October 12, 1976
INVENTOR(S) : Berthold Richard Vogt It is certified that error appears in the above-identified patent and that said Letters Patent are hereby corrected as shown below:

```
Column 2, line 52, " "head-to-head " should read
  --"head-to-head"--.
Column 5, line 23, "anthemlmintic" should read --anthelmintic--.
Column 7, line 3, "7aa" should read --7a--.
Column 7, line 25, after "7a," second occurrence insert
  --7b,--.
Column 9, line 43, "(275 1 ml)" should read --(275 ml)--.
Column 10, line 25, "4A" should read --4A°--.
Column 11, line 48, "dimethoxyethylene" should read
  --dimethoxyethane--.
Column 11, line 64, "[1,2-d']" should read --[1,2-d:3,4-d']--.
Column 12, line 51, "[1,2-d:3,4-d'[" should read
  --[1,2-d:3,4-d']--.
```

Signed and Sealed this

Twenty-eighth Day of December 1976

[SEAL]

Attest:

RUTH C. MASON
*Attesting Officer*

C. MARSHALL DANN
*Commissioner of Patents and Trademarks*